(12) United States Patent
Aoki

(10) Patent No.: US 10,299,664 B2
(45) Date of Patent: May 28, 2019

(54) SOLID-STATE IMAGING DEVICE AND ENDOSCOPE SYSTEM

(71) Applicant: OLYMPUS CORPORATION, Hachioji-shi, Tokyo (JP)

(72) Inventor: Jun Aoki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/866,633

(22) Filed: Jan. 10, 2018

(65) Prior Publication Data

US 2018/0125341 A1 May 10, 2018

Related U.S. Application Data

(63) Continuation of application No. PCT/JP2015/076898, filed on Sep. 24, 2015.

(51) Int. Cl.
*H01L 27/14* (2006.01)
*A61B 1/04* (2006.01)
(Continued)

(52) U.S. Cl.
CPC ............ *A61B 1/04* (2013.01); *A61B 1/00096* (2013.01); *A61B 1/05* (2013.01); *G02B 5/20* (2013.01);
(Continued)

(58) Field of Classification Search
CPC ...... A61B 1/04; H04N 9/07; H01L 27/14636; H01L 27/146; G02B 5/20
See application file for complete search history.

(56) References Cited

U.S. PATENT DOCUMENTS

2005/0224841 A1\* 10/2005 Nakamura ........... H04N 5/3597
257/215
2009/0184387 A1 7/2009 Takeuchi
(Continued)

FOREIGN PATENT DOCUMENTS

JP  2009-111225 A  * 5/2009
JP  2009-168742 A    7/2009
(Continued)

OTHER PUBLICATIONS

International Search Report dated Nov. 24, 2015, issued in counterpart International Application No. PCT/JP2015/076898 (4 pages, including Japanese original and English translation).

*Primary Examiner* — Ahmed N Sefer
(74) *Attorney, Agent, or Firm* — Westerman, Hattori, Daniels & Adrian, LLP

(57) ABSTRACT

The solid-state imaging device includes a semiconductor layer, an electrode, a wiring layer, a plurality of filters, an input terminal, and a voltage generation circuit. The voltage generation circuit generates a first voltage and a second voltage. The plurality of filters include a first filter and a second filter. The light transmittance of the first filter has a peak in a wavelength range corresponding to blue. The light transmittance of the second filter has a peak at a wavelength of 450 nm or more, and in the second filter, the transmittance of light having a wavelength of 450 nm or less is greater than the minimum value of the transmission of light having a wavelength longer than 450 nm. The first voltage and the second voltage are selectively applied to the electrode.

5 Claims, 10 Drawing Sheets

(51) Int. Cl.
  *G02B 5/20* (2006.01)
  *H01L 27/146* (2006.01)
  *H04N 9/07* (2006.01)
  *A61B 1/00* (2006.01)
  *A61B 1/05* (2006.01)
  *G02B 23/24* (2006.01)

(52) U.S. Cl.
  CPC ......... *G02B 5/201* (2013.01); *G02B 23/2484* (2013.01); *H01L 27/14* (2013.01); *H01L 27/146* (2013.01); *H01L 27/14636* (2013.01); *H04N 9/07* (2013.01)

(56) References Cited

U.S. PATENT DOCUMENTS

| | | |
|---|---|---|
| 2010/0140733 A1 | 6/2010 | Lee et al. |
| 2012/0217601 A1 | 8/2012 | Miyanami |
| 2014/0084410 A1* | 3/2014 | Okigawa ........... H01L 27/14636 257/447 |
| 2014/0104403 A1* | 4/2014 | Ogasawara ........ G02B 23/2461 348/68 |
| 2014/0339665 A1* | 11/2014 | Tani ....................... G02B 5/201 257/432 |
| 2014/0346629 A1* | 11/2014 | Naya ....................... H04N 9/07 257/432 |
| 2015/0091115 A1* | 4/2015 | Lin ..................... H01L 27/1463 257/432 |
| 2015/0092034 A1 | 4/2015 | Iwane |

FOREIGN PATENT DOCUMENTS

| | | |
|---|---|---|
| JP | 2009-182349 A | 8/2009 |
| JP | 2012-170639 A | 9/2012 |
| JP | 2012-175050 A | 9/2012 |
| JP | 2015-66063 A | 4/2015 |
| WO | 2012/165255 A1 | 12/2012 |

* cited by examiner

SOLID-STATE IMAGING DEVICE AND ENDOSCOPE SYSTEM

This is a continuation application based on International Patent Application No. PCT/JP2015/076898, filed Sep. 24, 2015, the content of which is incorporated herein by reference.

BACKGROUND OF THE INVENTION

Field of the Invention

The present invention relates to a solid-state imaging device and an endoscope system.

Description of Related Art

A technology which enables observation of blood vessels in a mucosal surface layer using narrowband light having a wavelength of about 410 nm has been disclosed as shown in Japanese Unexamined Patent Application, First Publication No. 2012-170639. It is possible to obtain images in which blood vessels are emphasized by irradiating blood vessels with narrowband light which is easily absorbed by hemoglobin in the blood. Three-color images and narrowband-light images are obtained, for example, using a solid-state imaging device (an image sensor) in which pixels corresponding to visible light of three colors, red (R), green (G), and blue (B), are arranged.

The arrangement of color filters in pixels in the solid-state imaging device which can obtain three-color images is, for example, a Bayer pattern. FIG. 14 shows a unit array F10 of color filters constituting a Bayer pattern. As shown in FIG. 14, the unit array F10 has one red color filter Fr10, two green color filters Fg10, and one blue color filter Fb10. The unit array F10 shown in FIG. 14 is arranged two-dimensionally in the solid-state imaging device.

FIG. 15 shows the spectral transmission characteristics of color filters of three colors. In the graphs shown in FIG. 15, the horizontal axis represents the wavelength and the vertical axis represents the transmittance of the color filters. The graph Gr20 shows the spectral transmission characteristics of the red color filter. The graph Gg20 shows the spectral transmission characteristics of the green color filter. The graph Gb20 shows the spectral transmission characteristics of the blue color filter. The red color filter has a transmittance peak PKr20 at a wavelength near 610 nm corresponding to a red wavelength. The green color filter has a transmittance peak PKg20 at a wavelength near 540 nm corresponding to a green wavelength. The blue color filter has a transmittance peak PKb20 at a wavelength near 450 nm corresponding to a blue wavelength.

The transmittance of the blue color filter is high at 410 nm which is a wavelength of narrowband light. On the other hand, the transmittance of each of the red and green color filters is low at 410 nm. Therefore, narrowband light is likely to be detected only at pixels having blue color filters and is unlikely to be detected at pixels having red and green color filters.

The resolution of narrowband light images is low because narrowband light is unlikely to be detected at pixels having red and green color filters. In order to improve the resolution of narrowband light images, it is desirable that each of the red and green color filters have transparency to the wavelength of narrowband light. However, when a subject is irradiated with white light, red, green, and narrowband light are detected at pixels, thereby lowering the color resolution of color images. Therefore, it is conceivable to use red color filters having a steep peak transmittance at the wavelength of narrowband light. Similarly, it is conceivable to use green color filters having a steep peak transmittance at the wavelength of narrowband light.

FIG. 16 shows the spectral transmission characteristics of a green color filter having a steep peak transmittance at the wavelength of narrowband light. In the graph Gg21 shown in FIG. 16, the horizontal axis represents the wavelength and the vertical axis represents the transmittance of the color filter. The color filter has a transmittance peak PKg21 at a wavelength near 540 nm corresponding to a green wavelength. The color filter also has a transmittance peak PKg22 at a wavelength near 410 nm corresponding to the wavelength of narrowband light.

When a subject is irradiated with narrowband light, the narrowband light passes through the color filter due to the spectral transmission characteristics thereof near the peak PKg22. Therefore, the pixel can detect the narrowband light. On the other hand, when the subject is irradiated with white light, green light passes through the color filter due to the spectral transmission characteristics thereof near the peak PKg21. Therefore, the pixel can detect the green light. When the subject is irradiated with white light, narrowband light also passes through the color filter. Deterioration of the color resolution of color images is suppressed since a range of wavelengths having transparency near the peak PKg22 is narrow.

SUMMARY OF THE INVENTION

According to a first aspect of the present invention, a solid-state imaging device is a backside illumination type. The solid-state imaging device includes a semiconductor layer, an electrode, a wiring layer, a plurality of filters, an input terminal, and a voltage generation circuit. The semiconductor layer has a first surface, a second surface, and a plurality of photoelectric conversion elements. The electrode is disposed on the first surface. The wiring layer is laminated on the second surface of the semiconductor layer. The plurality of filters are arranged on the first surface side at positions corresponding to the plurality of photoelectric conversion elements. A reference voltage is input to the input terminal from the outside. The voltage generation circuit is configured to generate a first voltage and a second voltage on the basis of the reference voltage input to the input terminal. The plurality of filters include a first filter and a second filter. The light transmittance of the first filter has a peak in a wavelength range corresponding to blue. The light transmittance of the second filter has a peak at a wavelength of 450 nm or more, and in the second filter, the transmittance of light having a wavelength of 450 nm or less is greater than a minimum value of the transmittance of light having a wavelength longer than 450 nm. The first voltage and the second voltage are selectively applied to the electrode. The second voltage differs from the first voltage. The voltage generation circuit is configured to generate the second voltage to cause the photoelectric conversion elements to have a higher sensitivity to light having a wavelength of 450 nm or less, compared to when the first voltage is applied to the electrode.

According to a second aspect of the present invention, in the first aspect, a potential in a cross section of the semiconductor layer may have a first distribution when the first voltage is applied to the electrode. The potential in the cross section of the semiconductor layer may have a second distribution when the second voltage is applied to the electrode. In a first region of the cross section of the semiconductor layer, the potential at a peak of the first distribution may be greater than the potential at a peak of the second distribution. The first region may be a region in which a distance from the first surface is less than 0.3 μm.

According to a third aspect of the present invention, in the second aspect, a material constituting the semiconductor layer may include silicon. In the first distribution, a gradient of a variation of the potential in a second region of the cross section of the semiconductor layer may be greater than a gradient of a variation of the potential in a third region. The second region may be a region in which the distance is greater than a first distance at the peak of the first distribution and is less than 0.3 μm. The third region may be a region between the first surface and the photoelectric conversion elements in which the distance is 0.3 μm or more.

According to a fourth aspect of the present invention, in the first aspect, a trench may be arranged on the first surface side of the semiconductor layer in a region corresponding to a boundary between the first filter and the second filter.

According to a fifth aspect of the present invention, an endoscope system includes a solid-state imaging device, an illumination device, and a control device. The solid-state imaging device includes a semiconductor layer, an electrode, a wiring layer, and a plurality of filters. The semiconductor layer has a first surface, a second surface, and a plurality of photoelectric conversion elements. The electrode is disposed on the first surface. The wiring layer is laminated on the second surface of the semiconductor layer. The plurality of filters are arranged on the first surface side at positions corresponding to the plurality of photoelectric conversion elements. The plurality of filters include a first filter and a second filter. The light transmittance of the first filter has a peak in a wavelength range corresponding to blue. The light transmittance of the second filter has a peak at a wavelength of 450 nm or more, and in the second filter, the transmittance of light having a wavelength of 450 nm or less is greater than a minimum value of the transmittance of light having a wavelength longer than 450 nm. A first voltage and a second voltage are selectively applied to the electrode. The second voltage differs from the first voltage. The illumination device is configured to generate white light and narrowband light having a wavelength shorter than 450 nm. The control device is configured to control a voltage that is applied to the electrode according to light generated by the illumination device. The first voltage is applied to the electrode when the illumination device generates the white light. The second voltage is applied to the electrode when the illumination device generates the narrowband light. The second voltage is applied to the electrode to cause the photoelectric conversion elements to have a higher sensitivity to light having a wavelength of 450 nm or less, compared to when the first voltage is applied to the electrode.

According to a sixth aspect of the present invention, in the fifth aspect, a potential in a cross section of the semiconductor layer may have a first distribution when the first voltage is applied to the electrode. The potential in the cross section of the semiconductor layer may have a second distribution when the second voltage is applied to the electrode. In a first region of the cross section of the semiconductor layer, the potential at a peak of the first distribution may be greater than the potential at a peak of the second distribution. The first region may be a region in which a distance from the first surface is less than 0.3 μm.

According to a seventh aspect of the present invention, in the sixth aspect, a material constituting the semiconductor layer may include silicon. In the first distribution, a gradient of a variation of the potential in a second region of the cross section of the semiconductor layer may be greater than a gradient of a variation of the potential in a third region of the cross section of the semiconductor layer. The second region may be a region in which the distance is greater than a first distance at the peak of the first distribution and is less than 0.3 μm. The third region may be a region between the first surface and the photoelectric conversion elements in which the distance is 0.3 μm or more.

DETAILED DESCRIPTION OF THE INVENTION

Embodiments of the present invention will be described with reference to the drawings.
(First Embodiment)

Figure 1:
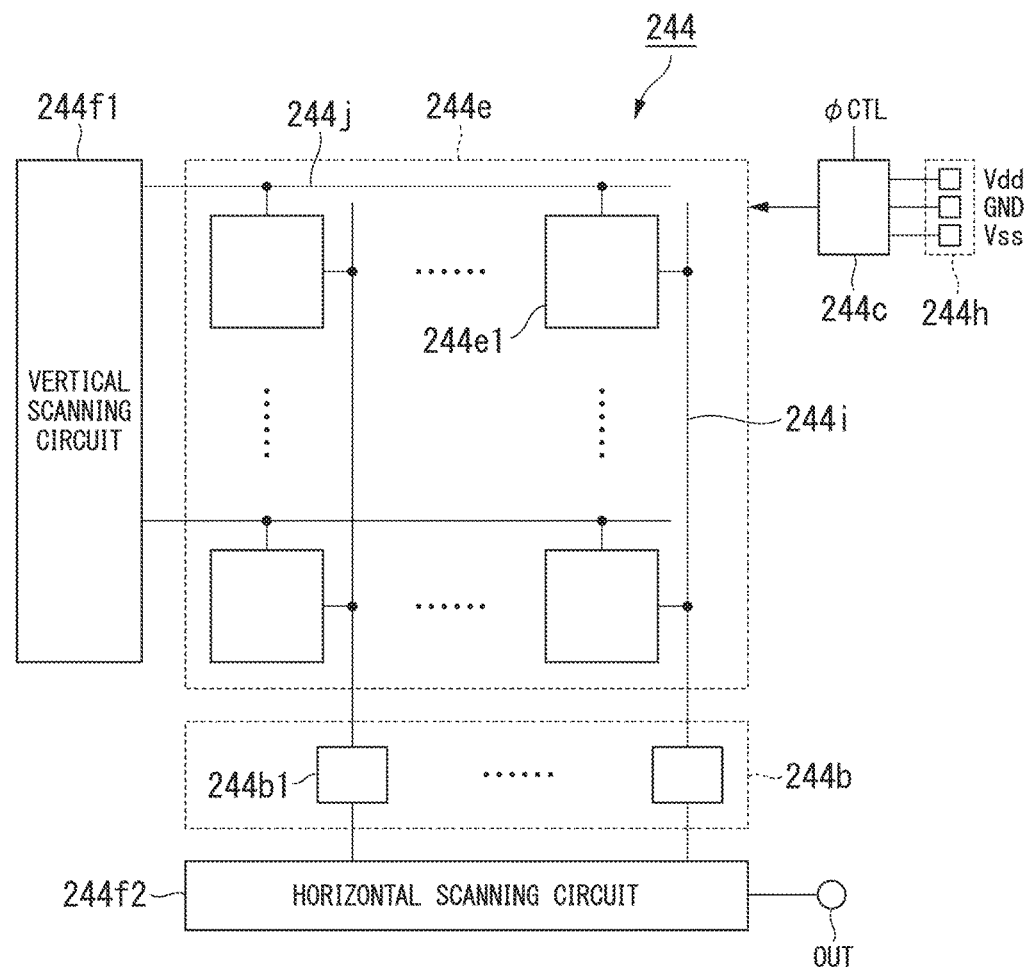
FIG. 1 is a block diagram showing a configuration of a solid-state imaging device according to a first embodiment of the present invention.

FIG. 1 shows a configuration of a solid-state imaging device 244 according to a first embodiment of the present invention. As shown in FIG. 1, the solid-state imaging device 244 includes a light receiving unit 244e (a pixel unit), an input terminal 244h, a voltage generation circuit 244c, a vertical scanning circuit 244f1, a horizontal scanning circuit 244f2, and a signal processing unit 244b. For example, the light receiving unit 244e, the input terminal 244h, the voltage generation circuit 244c, the vertical scanning circuit 244f1, the horizontal scanning circuit 244f2, and the signal processing unit 244b are arranged on the same substrate.

The light receiving unit 244e has a plurality of pixels 244e1 arranged in a matrix. In FIG. 1, a reference numeral of one pixel 244e1 is shown as a representative. Each of the plurality of pixels 244e1 generates an imaging signal corresponding to the amount of light incident on the pixel 244e1. Each of the plurality of pixels 244e1 is connected to a vertical signal line 244i. A plurality of vertical signal lines 244i are arranged. In FIG. 1, a reference numeral of one vertical signal line 244i is shown as a representative. The plurality of vertical signal lines 244i are arranged respectively for the columns of the array of the plurality of pixels 244e1. Each of the plurality of pixels 244e1 outputs the generated imaging signal to the corresponding vertical signal line 244i.

Each of the plurality of pixels 244e1 is connected to a control signal line 244j. A plurality of control signal lines 244j are arranged. In FIG. 1, a reference numeral of one control signal line 244j is shown as a representative. The plurality of control signal lines 244j are arranged respectively for the rows of the array of the plurality of pixels 244e1. Each of the plurality of control signal lines 244j is connected to the vertical scanning circuit 244f1. Control signals for controlling the operation of the plurality of pixels 244e1 are output from the vertical scanning circuit 244f1 to the control signal lines 244j.

The vertical scanning circuit 244f1 generates control signals for controlling the operation of the plurality of pixels 244e1. The vertical scanning circuit 244f1 generates control signals corresponding respectively to the rows of the array of the plurality of pixels 244e1. The vertical scanning circuit 244f1 outputs the generated control signals to the control signal lines 244j.

The signal processing unit 244b has a plurality of signal processing circuits 244b1. The signal processing circuits 244b1 are arranged respectively for the columns of the array of the plurality of pixels 244e1. The signal processing circuits 244b1 are connected to the vertical signal lines 244i. The signal processing circuits 244b1 perform signal processing such as noise removal on the imaging signals output to the vertical signal lines 244i.

The imaging signals processed by the signal processing circuits 244b1 are input to the horizontal scanning circuit 244f2. The horizontal scanning circuit 244f2 sequentially selects the columns of the array of the plurality of pixels 244e1. An imaging signal corresponding to a column selected by the horizontal scanning circuit 244f2 is output from the solid-state imaging device 244 through an output terminal OUT.

The voltage generation circuit 244c generates a plurality of voltages on the basis of reference voltages (power supply voltages) input to the input terminal 244h. A first reference voltage Vdd, a second reference voltage GND, and a third reference voltage Vss are input from an external power supply to the input terminal 244h. The first reference voltage Vdd is, for example, a positive voltage. The second reference voltage GND is, for example, ground. The third reference voltage Vss is, for example, a negative voltage. The plurality of voltages generated by the voltage generation circuit 244c are voltages between the second reference voltage GND and the third reference voltage Vss. The plurality of voltages generated by the voltage generation circuit 244c may include at least one of the second reference voltage GND and the third reference voltage Vss. The plurality of voltages generated by the voltage generation circuit 244c include a first voltage and a second voltage. The first voltage and the second voltage differ from each other. The voltage generation circuit 244c selectively outputs a plurality of voltages including the first voltage and the second voltage. A control signal φCTL is input to the voltage generation circuit 244c. The voltage generation circuit 244c switches the voltages output from the voltage generation circuit 244c on the basis of the control signal φCTL.

Figure 2:
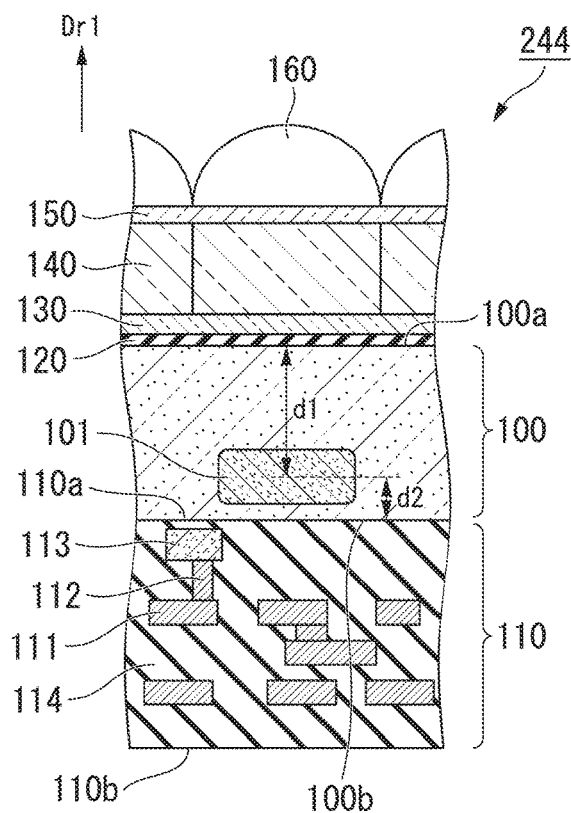
FIG. 2 is a cross-sectional view of the solid-state imaging device according to the first embodiment of the present invention.

FIG. 2 shows a partial cross section of the solid-state imaging device 244. The solid-state imaging device 244 includes a semiconductor layer 100, a wiring layer 110, an insulating layer 120, a transparent electrode 130, color filters 140, a resin layer 150, and microlenses 160. The solid-state imaging device 244 is a backside illumination type solid-state imaging device.

The dimensions of the portions constituting the solid-state imaging device 244 are not the same as the dimensions shown in FIG. 2. The dimensions of the portions constituting the solid-state imaging device 244 may be arbitrary. The same is also true for the dimensions in the cross-sectional views other than FIG. 2.

The semiconductor layer 100 and the wiring layer 110 are laminated in a thickness direction Dr1 of the semiconductor layer 100. The thickness direction Dr1 of the semiconductor layer 100 is perpendicular to a surface 100a of the semiconductor layer 100. The semiconductor layer 100 and the wiring layer 110 are in contact with each other. The semiconductor layer 100 and the wiring layer 110 constitute a substrate.

The semiconductor layer 100 is made of a semiconductor material. For example, the semiconductor material is at least one of silicon (Si) and germanium (Ge). The semiconductor layer 100 has the surface 100a (first surface) and a surface 100b (second surface). The surface 100a of the semiconductor layer 100 is a back surface of the semiconductor layer 100. The surface 100a of the semiconductor layer 100 is in contact with the insulating layer 120. The surface 100a of the semiconductor layer 100 is a main surface of the substrate. The main surface of the substrate is a relatively wide surface among a plurality of surfaces constituting the periphery of the substrate. The surface 100b of the semiconductor layer 100 is in contact with the wiring layer 110.

The semiconductor layer 100 has a plurality of photoelectric conversion elements 101 (photodiodes). In FIG. 2, one photoelectric conversion element 101 is shown as a representative. For example, the photoelectric conversion element 101 is made of a semiconductor material having an impurity concentration different from that of the semiconductor material constituting the semiconductor layer 100. The photoelectric conversion element 101 converts light into a signal. The distance d1 between the surface 100a of the semiconductor layer 100 and the photoelectric conversion element 101 is greater than the distance d2 between the surface 100b of the semiconductor layer 100 and the photoelectric conversion element 101. The photoelectric conversion elements 101, the color filters 140, and the microlenses 160 constitute the pixels 244e1.

The wiring layer 110 is laminated on the semiconductor layer 100 at the surface 100b of the semiconductor layer 100. The wiring layer 110 has a surface 110a and a surface 110b. The surface 110a of the wiring layer 110 is in contact with the semiconductor layer 100. The surface 110b of the wiring layer 110 is a main surface of the substrate.

The wiring layer 110 includes wirings 111, vias 112, gate electrodes 113, and an interlayer insulating film 114. In FIG.

2, a reference numeral of one wiring 111 is shown as a representative although there are a plurality of wirings 111. In FIG. 2, a reference numeral of one via 112 is shown as a representative although there are a plurality of vias 112.

The wiring 111 and the via 112 are each made of a conductive material. For example, the conductive material is a metal such as aluminum (Al) or copper (Cu). The wiring 111 and the via 112 may be made of different conductive materials. The wiring 111 is a thin film in which a wiring pattern is formed. The wiring 111 transmits a signal generated by the photoelectric conversion element 101. Only one layer of wirings 111 may be arranged or a plurality of layers of wirings 111 may be arranged. In the example shown in FIG. 2, two layers of wirings 111 are arranged. For example, in the periphery of the light receiving unit 244e, the wirings 111 are arranged in opening portions. Pads are arranged on the wirings 111 at the opening portions and are electrically connected to external wirings by wire bonding.

The vias 112 connect wirings 111 of different layers. The gate electrodes 113 are made of a semiconductor material. The semiconductor material constituting the gate electrodes 113 may be the same as the semiconductor material constituting the semiconductor layer 100. The interlayer insulating film 114 constitutes parts of the wiring layer 110 other than the wirings 111, the vias 112, and the gate electrodes 113. The interlayer insulating film 114 is made of a first insulating material. For example, the first insulating material is silicon dioxide (SiO2).

The insulating layer 120 is laminated on the semiconductor layer 100 at the surface 100a of the semiconductor layer 100. The insulating layer 120 is in contact with the semiconductor layer 100. The insulating layer 120 is made of a second insulating material. For example, the second insulating material is silicon dioxide (SiO2).

The transparent electrode 130 is laminated on the insulating layer 120. The transparent electrode 130 is in contact with the insulating layer 120. The transparent electrode 130 is made of a material having conductivity and transparency. For example, the transparent electrode 130 is at least one of indium tin oxide (ITO) and zinc oxide (ZnO). The first voltage and the second voltage generated by the voltage generation circuit 244c are selectively applied to the transparent electrode 130. For example, in the periphery of the light receiving unit 244e, the transparent electrode 130 is disposed in an opening portion. A pad is disposed on the transparent electrode 130 in the opening portion and is electrically connected to an external wiring by wire bonding. The insulating layer 120 need not be disposed and the transparent electrode 130 may be laminated on the semiconductor layer 100. That is, the transparent electrode 130 may be in contact with the semiconductor layer 100.

The solid-state imaging device 244 has a plurality of color filters 140. In FIG. 2, a reference numeral of one color filter 140 is shown as a representative. The plurality of color filters 140 are laminated on the transparent electrode 130. The plurality of color filters 140 are in contact with the transparent electrode 130.

The plurality of color filters 140 include a first filter and a second filter. The first filter is a blue color filter. The second filter is at least one of a red color filter and a green color filter. The blue color filter has a peak transmittance at a wavelength near 450 nm corresponding to a blue wavelength. The blue color filter transmits light in a wavelength range corresponding to blue. The red color filter has a peak transmittance at a wavelength near 610 nm corresponding to a red wavelength. The red color filter transmits light in a wavelength range corresponding to red. The green color filter has a peak transmittance at a wavelength near 540 nm corresponding to a green wavelength. The green color filter transmits light in a wavelength range corresponding to green.

The resin layer 150 is laminated on the color filters 140. The resin layer 150 is in contact with the color filters 140. The resin layer 150 is made of a resin material.

The solid-state imaging device 244 has a plurality of microlenses 160. In FIG. 2, a reference numeral of one microlens 160 is shown as a representative. The plurality of microlenses 160 are laminated on the resin layer 150. The plurality of microlenses 160 are in contact with the resin layer 150.

Light from a subject, which has passed through an imaging lens disposed optically in front of the solid-state imaging device 244, is incident on the microlenses 160. The microlenses 160 forms an image of light that has passed through the imaging lenses. The color filters 140 are arranged in regions corresponding to the microlenses 160. That is, the color filters 140 are arranged in regions through which light transmitted through the microlenses 160 passes. Light that has passed through the microlenses 160 is transmitted through the resin layer 150 and is then incident on the color filters 140. The color filters 140 transmit light in specific wavelength ranges.

Light transmitted through the color filters 140 passes through the transparent electrode 130 and the insulating layer 120 and is then incident on the semiconductor layer 100. Light is incident on the back surface, that is, the surface 100a of the semiconductor layer 100. In the semiconductor layer 100, the photoelectric conversion elements 101 are arranged in regions corresponding to the microlenses 160. In other words, the photoelectric conversion elements 101 are disposed in regions through which light transmitted through the microlenses 160 passes. Light incident on the semiconductor layer 100 is incident on the photoelectric conversion elements 101. The photoelectric conversion elements 101 convert the incident light into signals.

Figure 3:
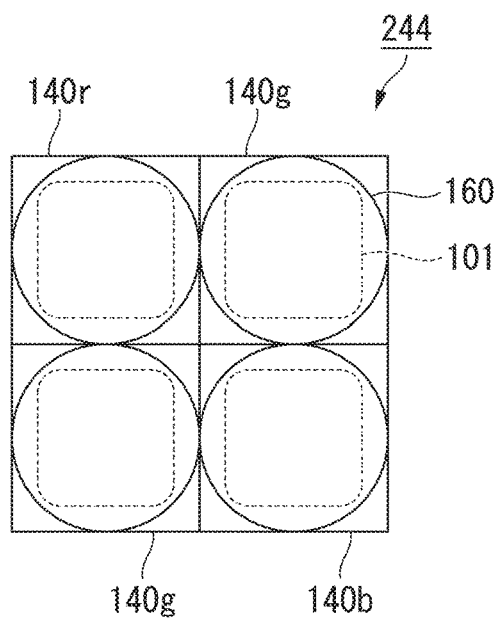
FIG. 3 is a plan view of the solid-state imaging device according to the first embodiment of the present invention.

FIG. 3 shows an arrangement of a plurality of photoelectric conversion elements 101, a plurality of color filters 140, and a plurality of microlenses 160. FIG. 3 shows the arrangement when the solid-state imaging device 244 is viewed in a direction perpendicular to the surface 100a of the semiconductor layer 100. That is, FIG. 3 shows the arrangement when the solid-state imaging device 244 is viewed from the front of a substrate constituting the solid-state imaging device 244. In FIG. 3, a reference numeral of one microlens 160 is shown as a representative. In FIG. 3, a reference numeral of one photoelectric conversion element 101 is shown as a representative.

The plurality of color filters 140 include color filters 140r, color filters 140g, and color filters 140b. The color filters 140r are red color filters. The color filters 140g are green color filters. The color filters 140b are blue color filters. FIG. 3 shows an example in which the arrangement of the color filters 140 in the pixels 244e1 in the solid-state imaging device 244 is a Bayer pattern.

Four color filters are shown in FIG. 3. The arrangement of the four color filters shown in FIG. 3 is a unit array of color filters constituting a Bayer pattern. As shown in FIG. 3, the unit array has one red color filter 140r, two green color filters 140g, and one blue color filter 140b. The unit array shown in FIG. 3 is arranged two-dimensionally in the light receiving unit 244e of the solid-state imaging device 244.

The plurality of photoelectric conversion elements 101, the plurality of color filters 140, and the plurality of microlenses 160 are arranged in a matrix. When the solid-state imaging device 244 is viewed in a direction perpendicular to the surface 100a of the semiconductor layer 100, each of the plurality of photoelectric conversion elements 101 overlaps one of the plurality of microlenses 160. One photoelectric conversion element 101 and one microlens 160 correspond to each other. When the solid-state imaging device 244 is viewed in a direction perpendicular to the surface 100a of the semiconductor layer 100, each of the plurality of photoelectric conversion elements 101 overlaps one of the plurality of color filters 140. One photoelectric conversion element 101 and one color filter 140 correspond to each other. When the solid-state imaging device 244 is viewed in a direction perpendicular to the surface 100a of the semiconductor layer 100, the center of the photoelectric conversion element 101 coincides with the center of the microlens 160 and the center of the photoelectric conversion element 101 coincides with the center of the color filter 140.

The transparent electrode 130 is omitted in FIG. 3. When the solid-state imaging device 244 is viewed in a direction perpendicular to the surface 100a of the semiconductor layer 100, the transparent electrode 130 is arranged to overlap the plurality of photoelectric conversion elements 101, the plurality of color filters 140, and the plurality of microlenses 160.

Figure 4:
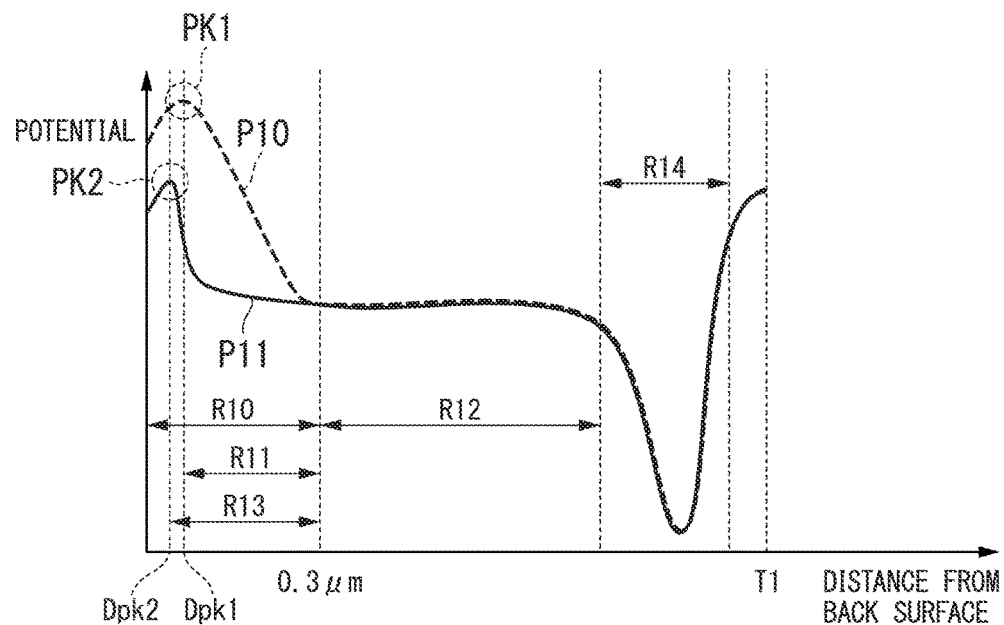
FIG. 4 is a graph showing the potential of a semiconductor layer in the solid-state imaging device according to the first embodiment of the present invention.

FIG. 4 shows a distribution of potential in a cross section of the semiconductor layer 100. FIG. 4 shows the potential distribution when the semiconductor material constituting the semiconductor layer 100 is silicon. FIG. 4 shows the potential distribution in a cross section passing through the photoelectric conversion element 101. In FIG. 4, the horizontal axis represents the distance from the surface 100a of the semiconductor layer 100, that is, the distance from the back surface. In FIG. 4, the vertical axis represents the potential.

A first distribution P10 and a second distribution P11 of the potential are shown in FIG. 4. The first distribution P10 shows a distribution of the potential in the cross section of the semiconductor layer 100 when the first voltage is applied to the transparent electrode 130. The second distribution P11 shows a distribution of the potential in the cross section of the semiconductor layer 100 when the second voltage is applied to the transparent electrode 130. The first distribution P10 and the second distribution P11 can be calculated by numerical calculation. A distance T1 at the right end of the first and second distributions P10 and P11 indicates the thickness of the semiconductor layer 100. For example, the thickness of the semiconductor layer 100 is 2.5 μm or more and 3.0 μm or less.

The first distribution P10 has a peak PK1 in a first region R10 in which the distance from the back surface is 0 μm or more and less than 0.3 μm. The second distribution P11 has a peak PK2 in the first region R10. The potential at the peak PK1 is greater than the potential at the peak PK2. At each distance in the first region R10, the potential indicated by the first distribution P10 is greater than the potential indicated by the second distribution P11.

In a second region R11, the potential indicated by the first distribution P10 steeply decreases as the distance from the back surface increases. The second region R11 is a region in which the distance from the back surface is greater than a first distance Dpk1 at the peak PK1 and is less than 0.3 μm. In a third region R12, the potential indicated by the first distribution P10 gradually changes as the distance from the back surface increases. The third region R12 is a region between the surface 100a of the semiconductor layer 100 and the photoelectric conversion element 101, and the distance from the surface 100a of the semiconductor layer 100 is 0.3 μm or more in the region. In the first distribution P10, the gradient of the variation of the potential in the second region R11 is greater than the gradient of the variation of the potential in the third region R12. The potential indicated by the first distribution P10 in the first region R10 is greater than the potential indicated by the first distribution P10 in the third region R12.

In a fourth region R13, the potential indicated by the second distribution P11 steeply decreases as the distance from the back surface increases. The fourth region R13 is a region in which the distance from the back surface is greater than a second distance Dpk2 at the peak PK2 and is less than 0.3 μm. In the third region R12, the potential indicated by the second distribution P11 gradually changes as the distance from the back surface increases. In the third region R12, the first distribution P10 and the second distribution P11 are almost the same. In the second distribution P11, the gradient of the variation of the potential in the fourth region R13 is greater than the gradient of the variation of the potential in the third region R12. The potential indicated by the second distribution P11 in the first region R10 is greater than the potential indicated by the second distribution P11 in the third region R12.

The potential indicated by each of the first distribution P10 and the second distribution P11 greatly drops in a region R14 in which the photoelectric conversion element 101 is disposed.

The potential in the semiconductor layer 100 is controlled by selectively applying the first voltage and the second voltage to the transparent electrode 130. Pairs of charges and holes are generated by light incident on the semiconductor layer 100. In a region in the semiconductor layer 100 in which the potential is high, charges and holes generated by light easily disappear through recombination. Therefore, the region with a high potential has low sensitivity to light. Among the light incident on the semiconductor layer 100, light having a relatively short wavelength generates charges in the first region R10 having a small distance from the back surface. Among the light incident on the semiconductor layer 100, about half of light having a wavelength of 450 nm generates charges in the first region R10 in which the distance from the back surface is less than 0.3 μm.

In the first distribution P10, the potential in the first region R10 is high and therefore charges generated by light having a short wavelength easily disappear. Therefore, when the first voltage is applied to the transparent electrode 130, charges generated in the first region R10 are unlikely to be accumulated in the photoelectric conversion element 101. On the other hand, the potential in the first region R10 in the second distribution P11 is smaller than the potential in the first region R10 in the first distribution P10. Therefore, when the second voltage is applied to the transparent electrode 130, charges generated in the first region R10 are easily accumulated in the photoelectric conversion element 101. That is, the spectral sensitivity characteristics of the photoelectric conversion element 101 can be controlled by controlling the potential in the semiconductor layer 100.

The difference between the peak PK1 of the first distribution P10 and the peak PK2 of the second distribution P11 increases as the difference between the first voltage and the second voltage increases. The region in which the potential of the first distribution P10 is greater than the potential of the second distribution P11 (the first region R10 in FIG. 4) becomes wider as the difference between the first voltage and the second voltage increases.

The distributions of the potential shown in FIG. 4 are those when the semiconductor layer 100 is made of P type silicon and the photoelectric conversion element 101 is made of an N type impurity region. When the semiconductor layer 100 is made of P type silicon and the photoelectric conversion element 101 is made of an N type impurity region, applying a lower voltage to the transparent electrode 130 produces a higher potential in a region having a small distance from the back surface. When the semiconductor layer 100 is made of P type silicon and the photoelectric conversion element 101 is made of an N type impurity region, the first voltage is smaller than the second voltage.

Distributions of the potential when the semiconductor layer 100 is made of N type silicon and the photoelectric conversion element 101 is made of a P type impurity region have the same tendency as the distributions shown in FIG. 4. When the semiconductor layer 100 is made of N type silicon and the photoelectric conversion element 101 is made of a P type impurity region, applying a higher voltage to the transparent electrode 130 produces a higher potential in a region having a small distance from the back surface. When the semiconductor layer 100 is made of N type silicon and the photoelectric conversion element 101 is made of a P type impurity region, the first voltage is greater than the second voltage.

Figure 5:
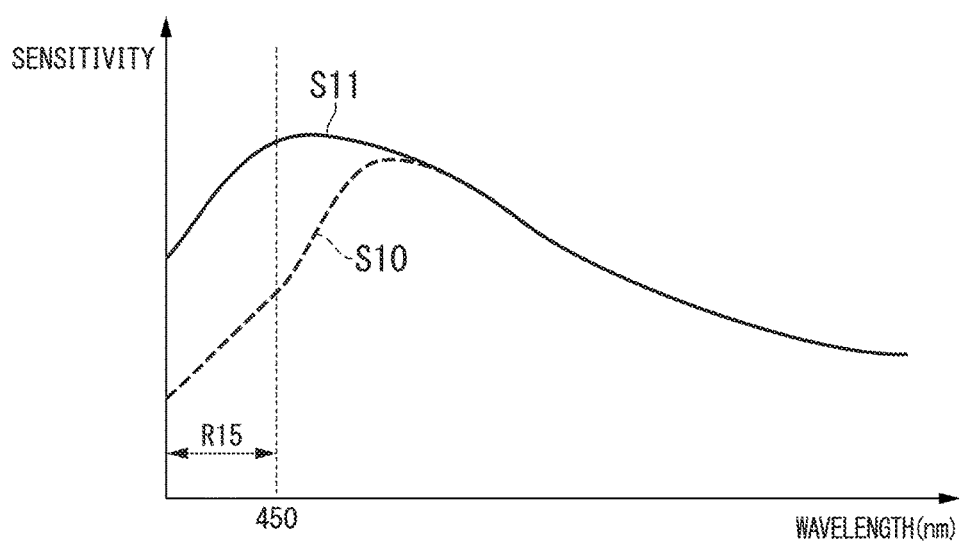
FIG. 5 is a graph showing spectral sensitivity characteristics of a photoelectric conversion element in the solid-state imaging device according to the first embodiment of the present invention.

FIG. 5 shows spectral sensitivity characteristics of the photoelectric conversion element 101. In the graphs shown in FIG. 5, the horizontal axis represents the wavelength and the vertical axis represents the sensitivity.

First characteristics S10 and second characteristics S11 of the spectral sensitivity are shown in FIG. 5. The first characteristics S10 indicate the spectral sensitivity characteristics of the photoelectric conversion element 101 when the first voltage is applied to the transparent electrode 130. The second characteristics S11 indicate the spectral sensitivity characteristics of the photoelectric conversion element 101 when the second voltage is applied to the transparent electrode 130. The first characteristics S10 and the second characteristics S11 can be calculated by numerical calculation.

In a region R15 in which the wavelength is 450 nm or less, the sensitivity indicated by the first characteristics S10 is smaller than the sensitivity indicated by the second characteristics S11. That is, the sensitivity of the photoelectric conversion element 101 to light having a wavelength of 450 nm or less when the first voltage is applied to the transparent electrode 130 is low compared to when the second voltage is applied to the transparent electrode 130. Therefore, when the first voltage is applied to the transparent electrode 130, charges generated by light having a wavelength of 450 nm or less are unlikely to be accumulated in the photoelectric conversion element 101.

When the subject is irradiated with white light, the first voltage is applied to the transparent electrode 130. At this time, the potential distribution of the semiconductor layer 100 is the first distribution P10. When the subject is irradiated with narrowband light having a wavelength shorter than 450 nm, the second voltage is applied to the transparent electrode 130. At this time, the potential distribution of the semiconductor layer 100 is the second distribution P11. For example, the wavelength of narrowband light is 390 nm or more and 445 nm or less.

When the subject is irradiated with white light and the first voltage is applied to the transparent electrode 130, the sensitivity of the photoelectric conversion element 101 to light having a wavelength of 450 nm or less is relatively low. Therefore, the solid-state imaging device 244 can obtain a signal with a high resolution for each of red, green, and blue light.

When the subject is irradiated with narrowband light having a wavelength shorter than 450 nm and the second voltage is applied to the transparent electrode 130, the sensitivity of the photoelectric conversion element 101 to light having a wavelength of 450 nm or less is relatively high. Therefore, the solid-state imaging device 244 can obtain a signal with a high resolution for narrowband light. Since a signal based on narrowband light is obtained from each of the photoelectric conversion elements 101 corresponding respectively to the color filters 140r, 140g, and 140b, the resolution of narrowband light images is equivalent to the resolution of color images of the three colors.

Therefore, the solid-state imaging device 244 can selectively detect narrowband light and light having a wavelength longer than the narrowband light. Since the sensitivity of the photoelectric conversion element 101 to light having a wavelength of 450 nm or less can be controlled, the color filters 140 may have transparency to light having a wavelength of 450 nm or less. Therefore, it is easy to manufacture the color filters 140.

Figure 6:
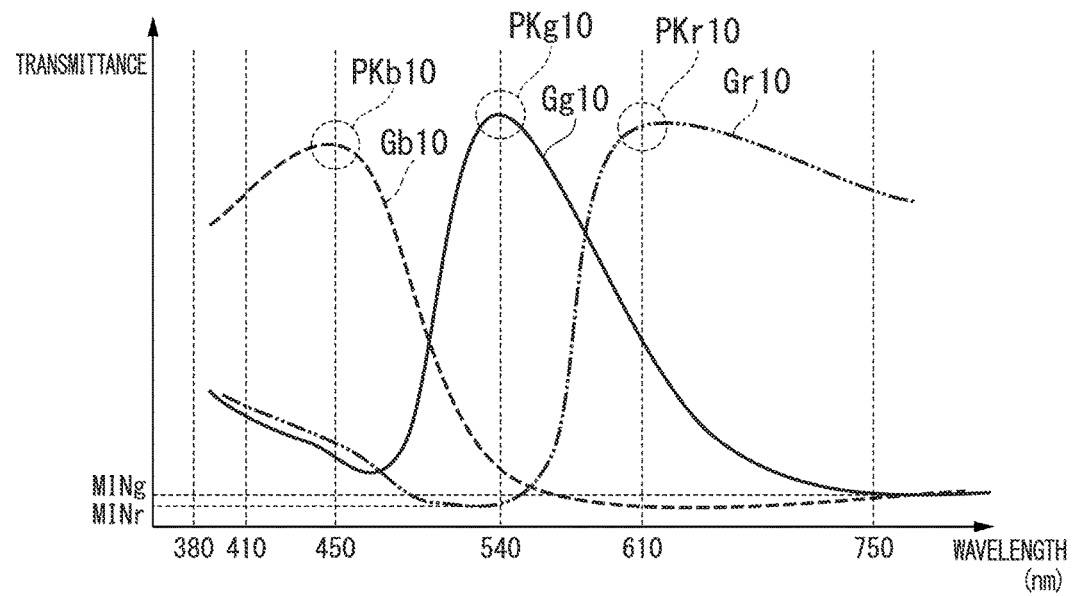
FIG. 6 is a graph showing spectral transmission characteristics of color filters in the solid-state imaging device according to the first embodiment of the present invention.
Figure 7:
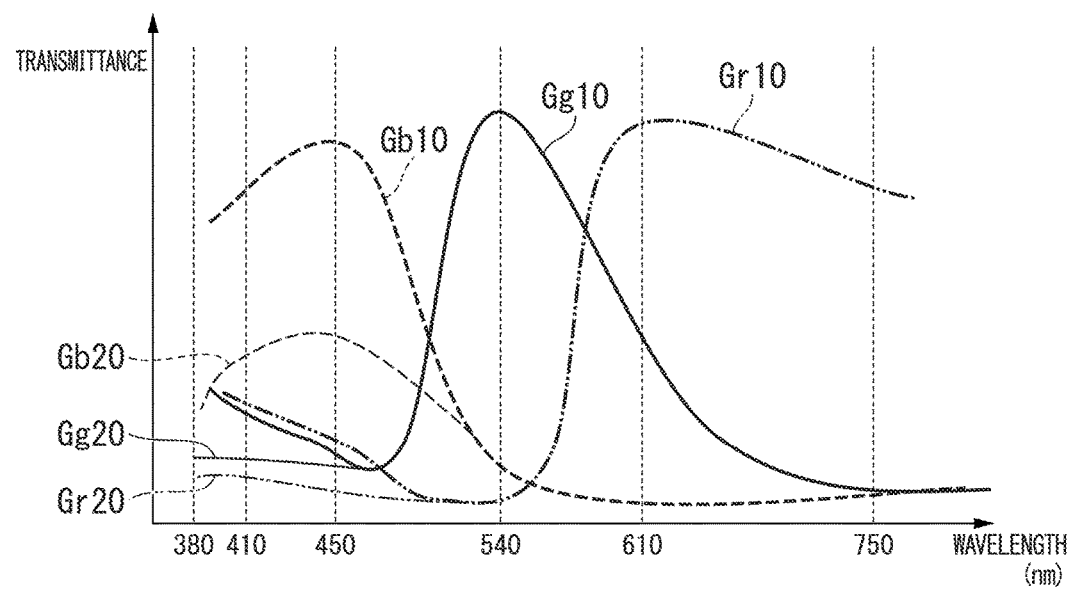
FIG. 7 is a graph showing spectral transmission characteristics of color filters in the solid-state imaging device according to the first embodiment of the present invention.

FIGS. 6 and 7 show spectral transmission characteristics of the color filters 140. In the graphs shown in FIGS. 6 and 7, the horizontal axis represents the wavelength and the vertical axis represents the transmittances of the color filters 140. The graph Gr10 shows the spectral transmission characteristics of the red color filter 140r. The graph Gg10 shows the spectral transmission characteristics of the green color filter 140g. The graph Gb10 shows the spectral transmission characteristics of the blue color filter 140b.

As shown in FIG. 6, the light transmittance of the color filter 140b has a peak PKb10 in a wavelength range corresponding to blue. A wavelength corresponding to the peak PKb10 is about 450 nm corresponding to a blue wavelength. The light transmittance of the color filter 140b has a peak PKb10 in a wavelength range of 380 nm or more and 540 nm or less. For example, the lower limit wavelength of the blue wavelength band, that is, the lower limit wavelength of the wavelength band of visible light is 380 nm. The color filter 140b has transparency to narrowband light.

As shown in FIG. 6, the light transmittance of the color filter 140r has a peak PKr10 in a wavelength range corresponding to red among the wavelengths of 450 nm or more. A wavelength corresponding to the peak PKr10 is about 610 nm corresponding to a red wavelength. The light transmittance of the color filter 140r has a peak PKr10 in a wavelength range of 540 nm or more and 750 nm or less. For example, the upper limit wavelength of the wavelength band of red, that is, the upper limit wavelength of the wavelength band of visible light is 750 nm. In the color filter 140r, the transmittance of light having a wavelength of 380 nm or more and 450 nm or less is greater than the minimum value MINr of the transmittance of light having a wavelength longer than 450 nm and less than or equal to 750 nm. That is, the color filter 140r has transparency to light having a wavelength of 380 nm or more and 450 nm or less. Therefore, the color filter 140r has transparency to narrowband light.

As shown in FIG. 6, the light transmittance of the color filter 140g has a peak PKg10 in a wavelength range corresponding to green among the wavelengths of 450 nm or more. A wavelength corresponding to the peak PKg10 is about 540 nm corresponding to a green wavelength. The light transmittance of the color filter 140g has a peak PKg10 in a wavelength range of 450 nm or more and 610 nm or less. In the color filter 140g, the transmittance of light having a wavelength of 380 nm or more and 450 nm or less is greater than the minimum value MINg of the transmittance of light having a wavelength longer than 450 nm and less than or equal to 750 nm. That is, the color filter 140g has transparency to light having a wavelength of 380 nm or more and 450 nm or less. Therefore, the color filter 140g has transparency to narrowband light.

When the subject is irradiated with white light and the first voltage is applied to the transparent electrode 130, the spectral transmission characteristics of the color filter 140b can be regarded as characteristics shown in a graph Gb20 in FIG. 7. With the characteristics shown in the graph Gb20, it is unlikely that light having a wavelength of 450 nm or less passes through the color filter 140b, compared with the characteristics shown in the graph Gb10.

When the subject is irradiated with white light and the first voltage is applied to the transparent electrode 130, the spectral transmission characteristics of the color filter 140r can be regarded as characteristics shown in a graph Gr20 in FIG. 7. With the characteristics shown in the graph Gr20, it is unlikely that light having a wavelength of 450 nm or less passes through the color filter 140r, compared with the characteristics shown in the graph Gr10.

When the subject is irradiated with white light and the first voltage is applied to the transparent electrode 130, the spectral transmission characteristics of the color filter 140g can be regarded as characteristics shown in a graph Gg20 in FIG. 7. With the characteristics shown in the graph Gg20, it is unlikely that light having a wavelength of 450 nm or less passes through the color filter 140g, compared with the characteristics shown in the graph Gg10.

The distance indicating the boundary of the first region R10 in which the distance from the surface 100a of the semiconductor layer 100 is less than 0.3 μm as shown in FIG. 4 need not be 0.3 μm. For example, the distance indicating the boundary of the first region R10 may be 0.12 μm. Among the light incident on the semiconductor layer 100, about half of light having a wavelength of 430 nm generates charges in a region in which the distance from the back surface is less than 0.12 μm.

The solid-state imaging device 244 is a backside illumination type solid-state imaging device as described above. The solid-state imaging device 244 includes a semiconductor layer 100, a transparent electrode 130 (an electrode), a wiring layer 110, a plurality of color filters 140 (filters), an input terminal 244h, and a voltage generation circuit 244c. The semiconductor layer 100 has a surface 100a (a first surface), a surface 100b (a second surface), and a plurality of photoelectric conversion elements 101. The transparent electrode 130 is disposed on the surface 100a of the semiconductor layer 100. The wiring layer 110 is laminated on the semiconductor layer 100 at the surface 100b of the semiconductor layer 100. The plurality of color filters 140 are arranged on the surface 100a side of the semiconductor layer 100 at positions corresponding to the plurality of photoelectric conversion elements 101. Reference voltages are input to the input terminal 244h from the outside. The voltage generation circuit 244c generates a first voltage and a second voltage on the basis of the reference voltages input to the input terminal 244h. The plurality of color filters 140 include a color filter 140b (a first filter) and color filters 140r and 140g (second filters). The light transmittance of the color filter 140b has a peak PKb10 in a wavelength range corresponding to blue. The light transmittances of the color filters 140r and 140g have peaks PKr10 and PKg10 in wavelengths of 450 nm or more and, in the color filters 140r and 140g, the transmittance of light having a wavelength of 450 nm or less is greater than the minimum values MINr and MINg of the transmittance of light having a wavelength longer than 450 nm. The first voltage and the second voltage are selectively applied to the transparent electrode 130. The second voltage differs from the first voltage.

When the first voltage is applied to the transparent electrode 130, the potential in the cross section of the semiconductor layer 100 has a first distribution P10. When the second voltage is applied to the transparent electrode 130, the potential in the cross section of the semiconductor layer 100 has a second distribution P11. In the first region R10, the potential at the peak PK1 of the first distribution P10 is greater than the potential at the peak PK2 of the second distribution P11. The first region R10 is a region in which the distance from the surface 100a of the semiconductor layer 100 is less than 0.3 μm.

The material constituting the semiconductor layer 100 includes silicon. The first distribution P10 has a peak PK1 in the first region R10. In the first distribution P10, the gradient of the variation of the potential in the second region R11 is greater than the gradient of the variation of the potential in the third region R12. The second region R11 is a region in which the distance from the surface 100a of the semiconductor layer 100 is greater than the first distance Dpk1 at the peak PK1 and is less than 0.3 μm. The third region R12 is a region between the surface 100a of the semiconductor layer 100 and the photoelectric conversion element 101 in which the distance from the surface 100a of the semiconductor layer 100 is 0.3 μm or more.

The solid state imaging device of each aspect of the present invention need not have a configuration corresponding to at least one of the vertical scanning circuit 244f1, the horizontal scanning circuit 244f2, and the signal processing unit 244b. The solid-state imaging device of each aspect of the present invention need not have a configuration corresponding to at least one of the insulating layer 120, the resin layer 150, and the microlenses 160.

In the first embodiment, by selectively applying the first voltage and the second voltage to the transparent electrode 130, the solid-state imaging device 244 can selectively detect narrowband light and light having a wavelength longer than the narrowband light.

(Second Embodiment)

Figure 8:
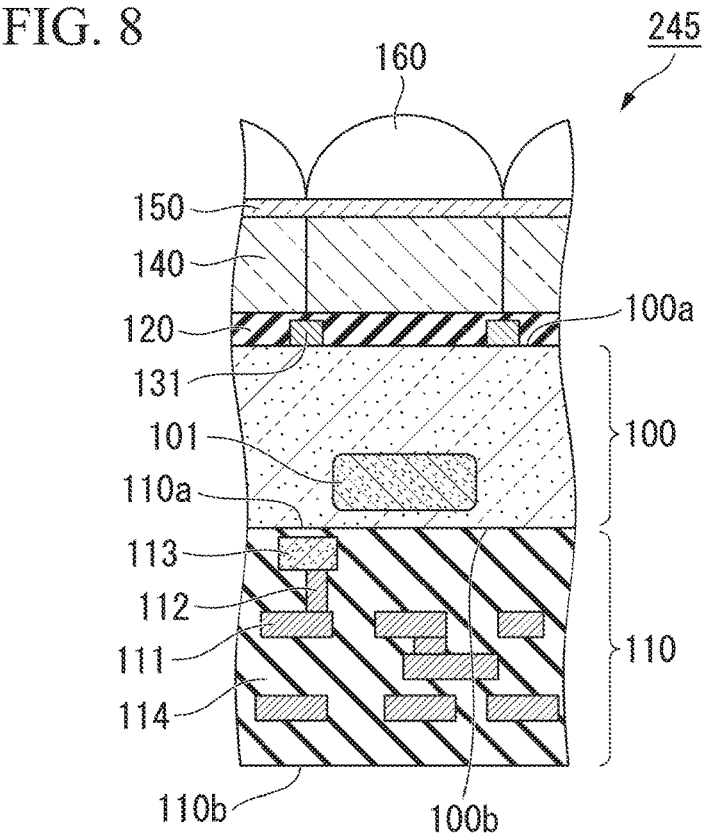
FIG. 8 is a cross-sectional view of a solid-state imaging device according to a second embodiment of the present invention.

In a second embodiment of the present invention, the solid-state imaging device 244 of the first embodiment is replaced with a solid-state imaging device 245 shown in FIG. 8.

FIG. 8 shows a partial cross section of the solid-state imaging device 245. The solid-state imaging device 245 includes a semiconductor layer 100, a wiring layer 110, an insulating layer 120, contact electrodes 131, color filters 140, a resin layer 150, and microlenses 160.

Differences of the configuration shown in FIG. 8 from the configuration shown in FIG. 2 will be described. The insulating layer 120 is laminated on the semiconductor layer 100. The insulating layer 120 is in contact with the semiconductor layer 100.

The contact electrodes 131 are buried in the insulating layer 120. Each of the contact electrodes 131 is made of a material having conductivity. For example, the contact electrode 131 is a metal such as tungsten (W). The contact electrodes 131 are disposed at positions at which they do not shield most of the light which has passed through the color filter 140 and will be incident on the photoelectric conversion element 101. A first voltage and a second voltage generated by the voltage generation circuit 244c are selectively applied to the contact electrodes 131. For example, the contact electrodes 131 are connected to wirings. The wirings are omitted in FIG. 8. In the periphery of the light receiving unit 244e, the wirings to which the contact electrodes 131 are connected are arranged in opening portions. Pads are arranged on the wirings in the opening portions and are electrically connected to external wirings by wire bonding.

The other points of the configuration shown in FIG. 8 are similar to those of the configuration shown in FIG. 2.

Figure 9:
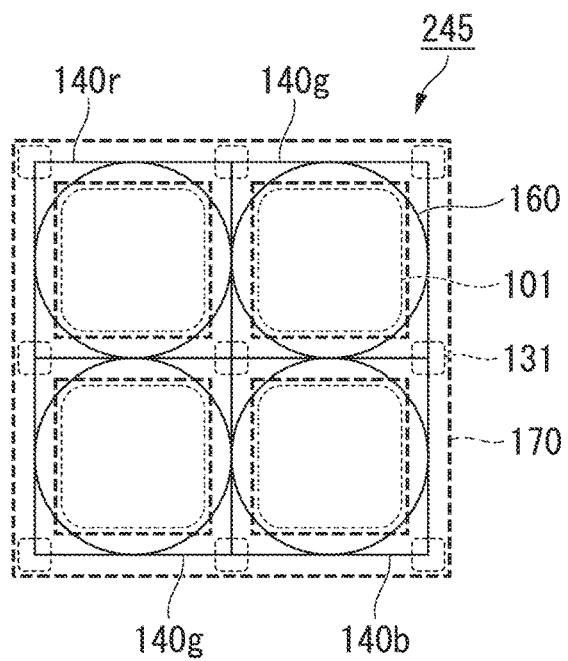
FIG. 9 is a plan view of the solid-state imaging device according to the second embodiment of the present invention.

FIG. 9 shows an arrangement of a plurality of photoelectric conversion elements 101, a plurality of color filters 140, a plurality of microlenses 160, and a plurality of contact electrodes 131. FIG. 9 shows the arrangement when the solid-state imaging device 245 is viewed in a direction perpendicular to the surface 100a of the semiconductor layer 100. That is, FIG. 9 shows the arrangement when the solid-state imaging device 245 is viewed from the front of a substrate constituting the solid-state imaging device 245.

Differences of the configuration shown in FIG. 9 from the configuration shown in FIG. 3 will be described. In FIG. 9, a reference numeral of one contact electrode 131 is shown as a representative. The plurality of contact electrodes 131 are arranged in a matrix. When the solid-state imaging device 245 is viewed in a direction perpendicular to the surface 100a of the semiconductor layer 100, the plurality of contact electrodes 131 are arranged around the microlenses 160 and the photoelectric conversion elements 101. Wirings 170 connected to the contact electrodes 131 are shown in FIG. 9. For example, the wirings 170 are buried in the insulating layer 120. The wirings 170 are omitted in FIG. 8.

The positions at which the plurality of contact electrodes 131 are arranged are not limited to those shown in FIG. 9. In FIG. 9, the pattern of the plurality of contact electrodes 131 is dot-like. The pattern of the plurality of contact electrodes 131 is not limited to that shown in FIG. 9. For example, the pattern of the plurality of contact electrodes 131 may be elongated and linear.

The other points of the configuration shown in FIG. 9 are similar to those of the configuration shown in FIG. 3.

In the second embodiment, by selectively applying the first voltage and the second voltage to the contact electrode 131, the solid-state imaging device 245 can selectively detect narrowband light and light having a wavelength longer than the narrowband light.

The transparent electrode 130 is made of a material having transparency. However, the transparent electrode 130 does not necessarily completely transmit light. On the other hand, the contact electrodes 131 are disposed at positions at which they do not shield most of the light which will be incident on the photoelectric conversion elements 101. By disposing the contact electrodes 131, light transmitted through the color filters 140 is likely to be incident on the photoelectric conversion elements 101.

(Third Embodiment)

Figure 10:
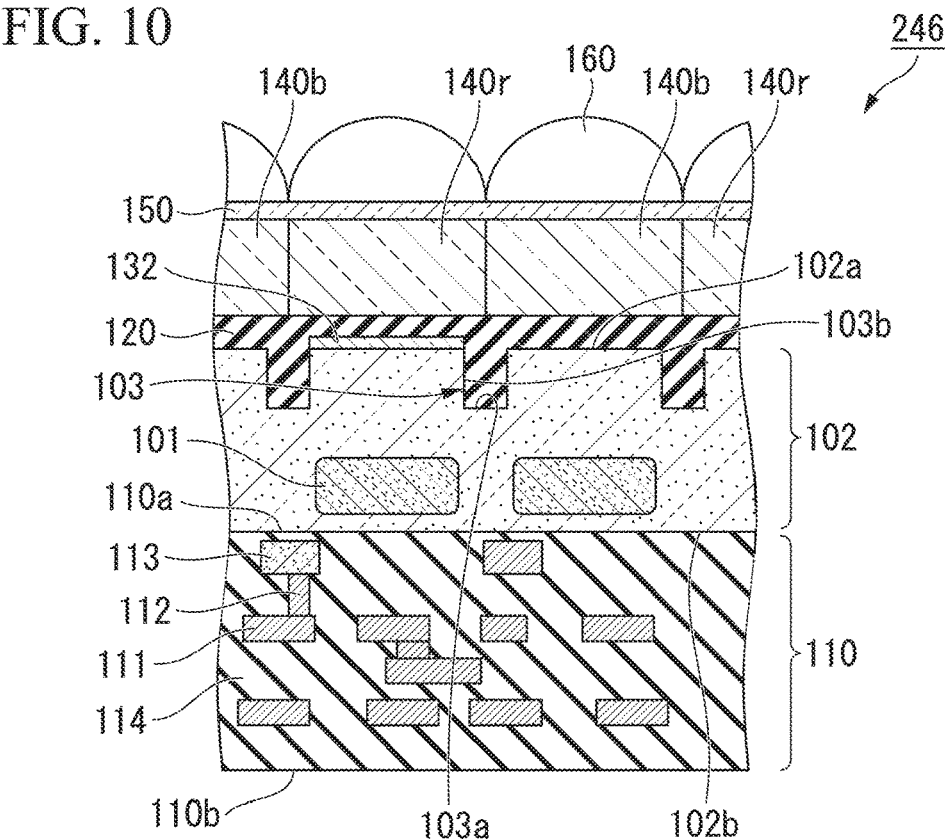
FIG. 10 is a cross-sectional view of a solid-state imaging device according to a third embodiment of the present invention.

In a third embodiment of the present invention, the solid-state imaging device 244 of the first embodiment is replaced with a solid-state imaging device 246 shown in FIG. 10.

FIG. 10 shows a partial cross section of the solid-state imaging device 246. The solid-state imaging device 246 includes a semiconductor layer 102, a wiring layer 110, an insulating layer 120, transparent electrodes 132, color filters 140, a resin layer 150, and microlenses 160.

Differences of the configuration shown in FIG. 10 from the configuration shown in FIG. 2 will be described. In FIG. 10, the semiconductor layer 100 in FIG. 2 is replaced with a semiconductor layer 102. The semiconductor layer 102 has a surface 102a (a first surface) and a surface 102b (a second surface). The surface 102a of the semiconductor layer 102 is the back surface of the semiconductor layer 102. The surface 102a of the semiconductor layer 102 is in contact with the insulating layer 120. The surface 102a of the semiconductor layer 102 is a main surface of the substrate. The surface 102b of the semiconductor layer 102 is in contact with the wiring layer 110.

The semiconductor layer 102 includes a plurality of photoelectric conversion elements 101 and trenches 103. In FIG. 10, a reference numeral of one trench 103 is shown as a representative although there are a plurality of trenches 103. The trenches 103 are arranged on the semiconductor layer 102 at the surface 102a of the semiconductor layer 102. The trenches 103 are formed by removing the semiconductor layer 102 from the surface 102a of the semiconductor layer 102.

In FIG. 10, blue color filters 140b and red color filters 140r are shown as the color filters 140. The trenches 103 are arranged in regions corresponding to boundaries between the color filters 140b and the color filters 140r. Each of the trenches 103 has a bottom surface 103a and a side wall 103b. The side wall 103b of the trench 103 is connected to the bottom surface 103a of the trench 103. For example, the distance between the surface 102a of the semiconductor layer 102 and the bottom surface 103a of the trench 103, that is, the depth of the trench 103 is 0.3 μm or more and is less than or equal to the thickness T1 of the semiconductor layer 100.

In FIG. 10, the transparent electrode 130 in FIG. 2 is replaced with a transparent electrode 132. The material constituting the transparent electrode 132 is similar to the material constituting the transparent electrode 130. Transparent electrodes 132 are disposed on the surface 102a of the semiconductor layer 102 in regions corresponding to the color filters 140r. Although not shown in FIG. 10, transparent electrodes 132 are also disposed in regions corresponding to the color filters 140g. No transparent electrodes 132 are disposed in regions corresponding to the color filters 140b. In other words, the transparent electrodes 132 are disposed in regions corresponding only to the color filters 140r and 140g among the color filters 140b, 140r, and 140g.

The trenches 103 are in contact with the insulating layer 120. That is, the trenches 103 are filled with an insulating material constituting the insulating layer 120.

The other points of the configuration shown in FIG. 10 are similar to those of the configuration shown in FIG. 2.

Figure 11:
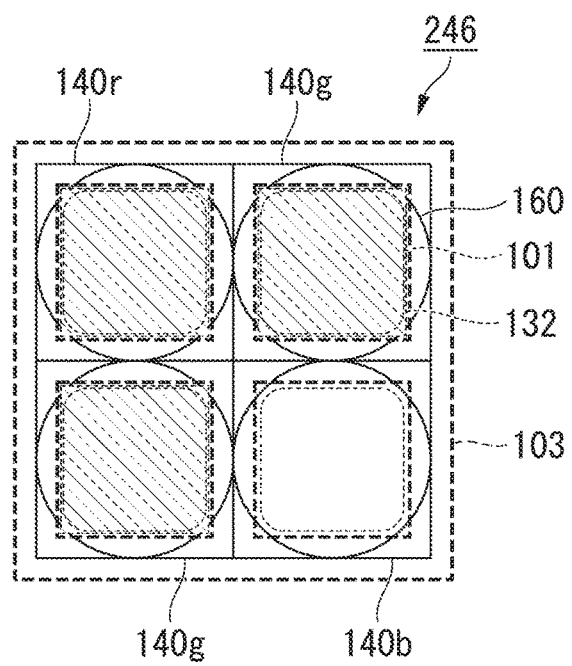
FIG. 11 is a plan view of the solid-state imaging device according to the third embodiment of the present invention.

FIG. 11 shows an arrangement of a plurality of photoelectric conversion elements 101, a plurality of color filters 140, a plurality of microlenses 160, and a plurality of transparent electrodes 132. FIG. 11 shows the arrangement when the solid-state imaging device 246 is viewed in a direction perpendicular to the surface 102a of the semiconductor layer 102. That is, FIG. 11 shows the arrangement when the solid-state imaging device 246 is viewed from the front of a substrate constituting the solid-state imaging device 246.

Differences of the configuration shown in FIG. 11 from the configuration shown in FIG. 3 will be described. In FIG. 11, a reference numeral of one transparent electrode 132 is shown as a representative. When the solid-state imaging device 246 is viewed in a direction perpendicular to the surface 102a of the semiconductor layer 102, each of the plurality of transparent electrodes 132 overlaps one of the plurality of microlenses 160. One transparent electrode 132 and one microlens 160 correspond to each other. When the solid-state imaging device 246 is viewed in a direction perpendicular to the surface 102a of the semiconductor layer 102, each of the plurality of transparent electrodes 132 overlaps one of the plurality of color filters 140r or one of the plurality of color filters 140g. One transparent electrode 132 corresponds to one color filter 140r or one color filter 140g. When the solid-state imaging device 246 is viewed in a direction perpendicular to the surface 102a of the semiconductor layer 102, the center of the transparent electrode 132 coincides with the center of the microlens 160 and the center of the transparent electrode 132 coincides with the center of the color filter 140r or the color filter 140g.

The trenches 103 are arranged in regions between adjacent color filters 140. Although the transparent electrodes 132 are connected to wirings, the wirings are omitted in FIGS. 10 and 11.

The other points of the configuration shown in FIG. 11 are similar to those of the configuration shown in FIG. 3.

As described above, the trenches 103 are arranged on the surface 100a side of the semiconductor layer 100 in regions corresponding to the boundaries between the color filters 140b and the color filters 140r or the color filters 140g.

First regions of the semiconductor layer 102 corresponding to the color filters 140b are separated from second regions of the semiconductor layer 102 corresponding to the color filters 140r or the color filters 140g by the trenches 103. Therefore, a voltage applied to the transparent electrodes 132 is unlikely to affect the first regions. As a result, it is possible to control the potential of regions of the semiconductor layer 102 corresponding to only the color filters 140r or the color filters 140g. That is, the potential of the first regions and the potential of the second regions can be controlled independently of each other.

When the first voltage and the second voltage are applied to the transparent electrodes 132, the potentials of the first regions of the semiconductor layer 102 corresponding to the color filters 140b are almost the same. That is, when the first voltage and the second voltage are applied to the transparent electrodes 132, the sensitivities of the photoelectric conversion elements 101 corresponding to the color filters 140b are almost the same. Therefore, when the subject is irradiated with white light and the first voltage is applied to the transparent electrodes 132, the sensitivities of the photoelectric conversion elements 101 corresponding to blue light do not decrease.

Transparent electrodes 132 may be disposed in first regions of the semiconductor layer 102 corresponding to the color filters 140b and second regions of the semiconductor layer 102 corresponding to the color filters 140r or the color filters 140g. A first voltage that is applied to the transparent electrodes 132 disposed in the first regions may differ from a first voltage that is applied to the transparent electrodes 132 arranged in the second regions. A second voltage that is applied to the transparent electrodes 132 disposed in the first regions may differ from a second voltage that is applied to the transparent electrodes 132 arranged in the second regions.

In the third embodiment, the solid-state imaging device 246 can selectively detect narrowband light and light having a wavelength longer than the narrowband light, similar to the first embodiment.

In the third embodiment, the trenches 103 are arranged. Therefore, the potential of the first regions of the semiconductor layer 102 corresponding to the color filters 140b and the potential of the second regions of the semiconductor layer 102 corresponding to the color filters 140r or the color filters 140g can be controlled independently of each other.

(Fourth Embodiment)

Figure 12:
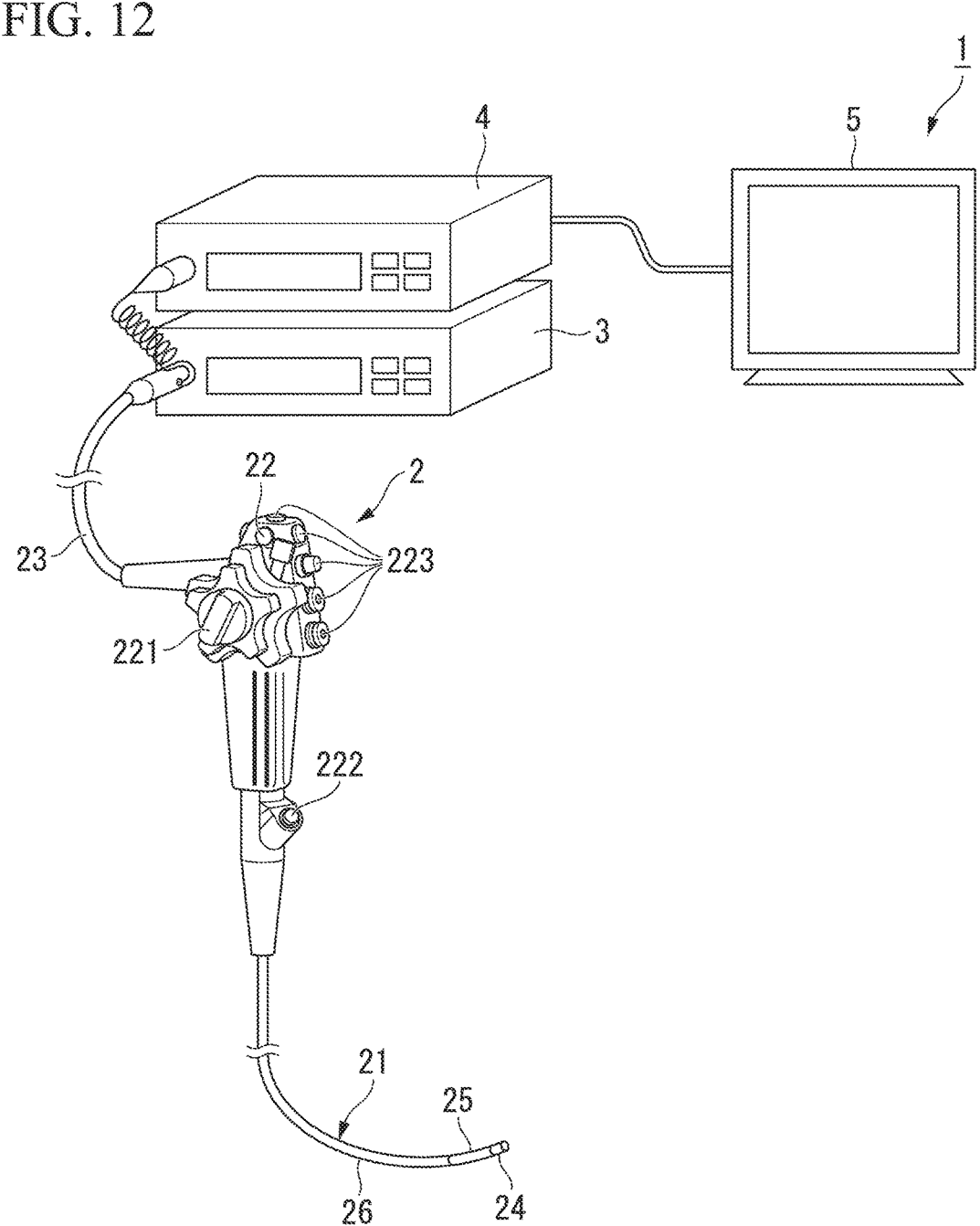
FIG. 12 is an overall view of an endoscope system according to a fourth embodiment of the present invention.

FIG. 12 shows an overall configuration of an endoscope system 1 according to a fourth embodiment of the present invention. The endoscope system 1 is a medical system that captures and displays internal images of a body cavity of a subject such as a patient. As shown in FIG. 1, the endoscope system 1 includes an endoscope 2, a light source device 3, a processing device 4, and a display device 5.

A distal end of the endoscope 2 is inserted into the body cavity of the subject. The endoscope 2 obtains an internal image of the subject. The light source device 3 generates illumination light which is emitted from the distal end of the endoscope 2. The processing device 4 performs predetermined image processing on the image obtained by the endoscope 2. The processing device 4 also controls the overall operation of the endoscope system 1. The display device 5 displays the image processed by the processing device 4.

The endoscope 2 includes an insertion portion 21, an operation unit 22, and a universal cord 23. The insertion portion 21 is flexible and has an elongated shape. The operation unit 22 is connected to the proximal end side of the insertion portion 21. The operation unit 22 receives inputs of various operations. The universal cord 23 is connected to the operation unit 22. The universal cord 23 can be attached to and detached from each of the light source device 3 and the processing device 4. The universal cord 23 incorporates various cables that are electrically connected to the light source device 3 and the processing device 4.

The insertion portion 21 has a distal end portion 24, a bending portion 25, and a flexible tube portion 26. The distal end portion 24 incorporates the solid-state imaging device 244 of the first embodiment. The bending portion 25 can bend in a plurality of directions. The flexible tube portion 26 is connected to the proximal end side of the bending portion 25. The flexible tube portion 26 is flexible and elongated.

The operation unit 22 includes a bending knob 221, a treatment instrument insertion portion 222, and a plurality of switches 223. The bending knob 221 is a knob for bending the bending portion 25 in a plurality of directions. The treatment instrument is inserted into the body cavity of the subject from the treatment instrument insertion portion 222. Operation instructions are input to the plurality of switches 223.

Figure 13:
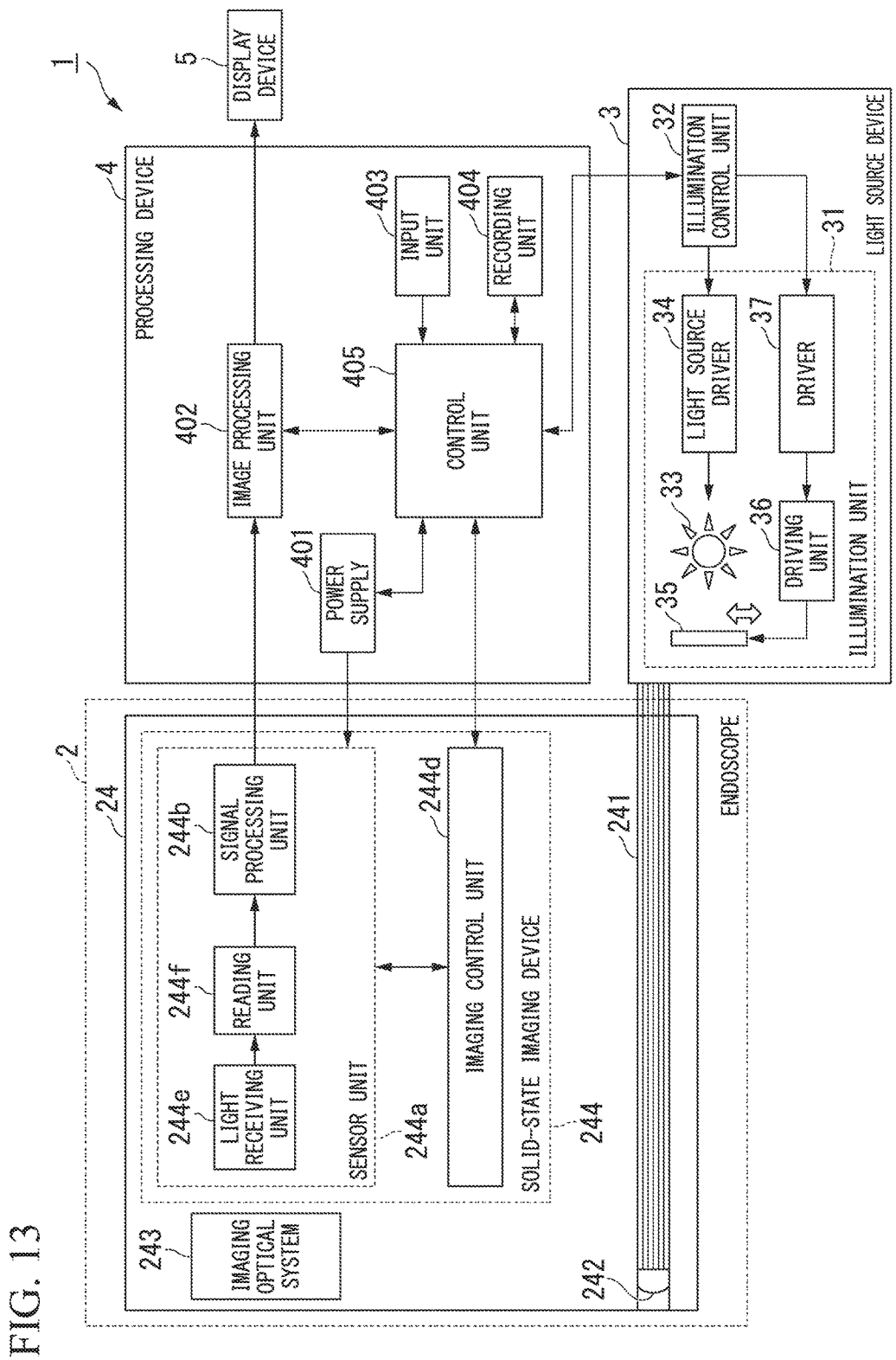
FIG. 13 is a block diagram showing an internal configuration of the endoscope system according to the fourth embodiment of the present invention.
Figure 14:
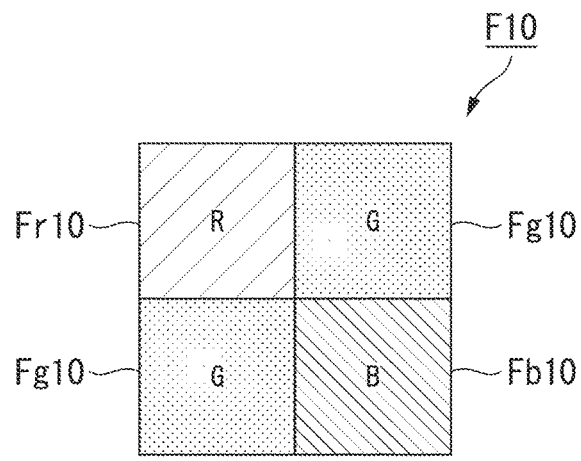
FIG. 14 is a reference diagram showing a unit array of color filters constituting a Bayer pattern.
Figure 15:
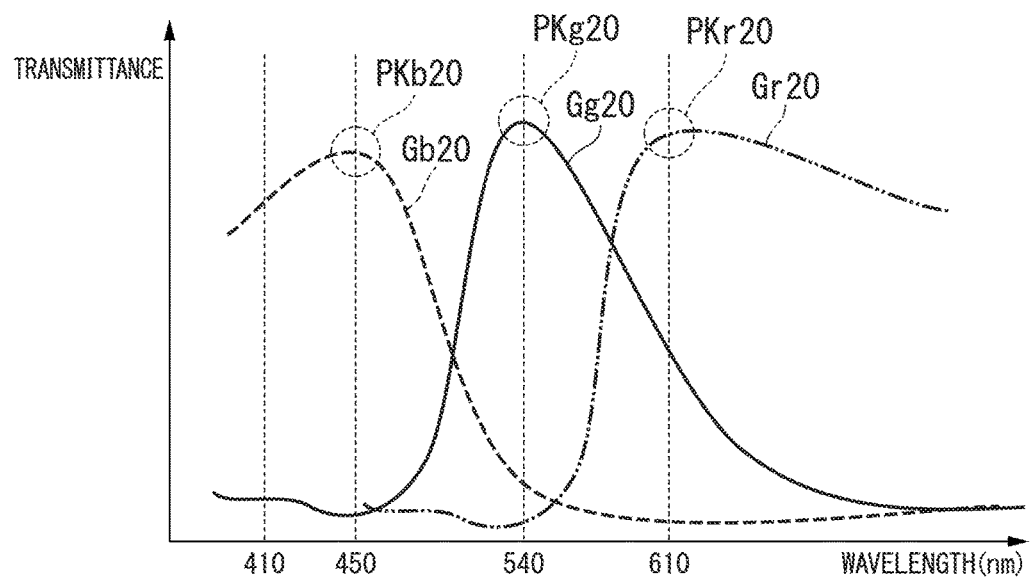
FIG. 15 is a graph showing spectral transmission characteristics of color filters.
Figure 16:
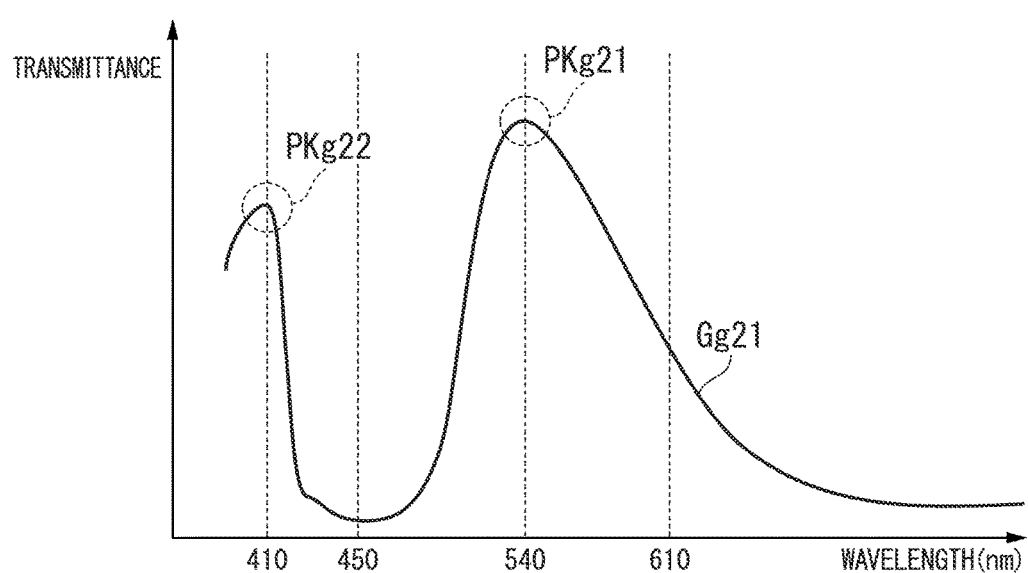
FIG. 16 is a graph showing spectral transmission characteristics of color filters.

FIG. 13 shows an internal configuration of the endoscope system 1. The distal end portion 24 includes a light guide 241, an illumination lens 242, an imaging optical system 243, and a solid-state imaging device 244. The light guide 241 is made of glass fiber or the like. The light guide 241 guides light generated by the light source device 3 to the distal end portion 24. The light guide 241 is incorporated in the universal cord 23. The illumination lens 242 is provided at a distal end of the light guide 241. The illumination lens 242 emits light transmitted through the light guide 241 to the outside. The imaging optical system 243 is disposed between a distal end surface of the distal end portion 24 and the light receiving unit 244e. The imaging optical system 243 has one or more lenses.

The solid-state imaging device 244 includes a sensor unit 244a and an imaging control unit 244d. The sensor unit 244a includes a light receiving unit 244e, a reading unit 244f, and a signal processing unit 244b. Descriptions of the light receiving unit 244e and the signal processing unit 244b will be omitted since they have already been described. The reading unit 244f corresponds to the vertical scanning circuit 244f1 and the horizontal scanning circuit 244f2. The imaging control unit 244d controls the operation of each part of the solid-state imaging device 244.

The light source device 3 includes an illumination unit 31 (an illumination device) and an illumination control unit 32. The illumination unit 31 selectively generates a plurality of beams of illumination light having different wavelength bands. The illumination unit 31 includes a light source 33, a light source driver 34, a switching filter 35, a driving unit 36, and a driver 37.

The light source 33 generates white light including light in respective wavelength bands of red, green, and blue. The white light generated by the light source 33 includes narrowband light. The white light generated by the light source 33 is guided to the distal end portion 24 via the switching filter 35 and the light guide 241. White light is emitted to the outside from the distal end portion 24. For example, the light source 33 is a white LED or a xenon lamp. The light source 33 need not be a single lamp. For example, the light source 33 may be a light source that includes an LED generating red light, an LED generating green light, and an LED generating blue light and that synthesizes and outputs light of the colors.

The light source driver 34 drives the light source 33 by supplying a current to the light source 33. The switching filter 35 transmits only narrowband light in a predetermined wavelength range among the white light generated by the light source 33. For example, the wavelength of the narrowband light is 390 nm or more and 445 nm or less. The illumination control unit 32 can switch between a state in which the switching filter 35 is inserted in the optical path of the white light generated by the light source 33 and a state in which the switching filter 35 is out of the optical path. When the switching filter 35 is disposed in the optical path of the white light, the switching filter 35 transmits only the narrowband light. Thus, the illumination unit 31 generates the narrowband light. When the switching filter 35 is out of the optical path, the illumination unit 31 generates white light.

The driving unit 36 includes a stepping motor and a DC motor. The driving unit 36 moves the switching filter 35. The driver 37 supplies a predetermined current to the driving unit 36.

The illumination control unit 32 controls the light source driver 34 to turn on or off the light source 33. The illumination control unit 32 also controls the driver 37 to move the switching filter 35. Thereby, the illumination control unit 32 controls the type (the wavelength band) of illumination light emitted from the illumination unit 31. That is, by controlling the state of the switching filter 35, the illumination control unit 32 switches the illumination light emitted from the illumination unit 31 to one of white light and narrowband light.

The processing device 4 includes a power supply 401, an image processing unit 402, an input unit 403, a recording unit 404, and a control unit 405 (a control device). The power supply 401 generates a voltage for driving the solid-state imaging device 244. The voltage generated by the power supply 401 is transmitted to the sensor unit 244*a*. The power supply 401 also generates a voltage for driving the light source device 3 and the processing device 4. The voltage generated by the power supply 401 is supplied to each part of the light source device 3 and the processing device 4.

The image processing unit 402 generates an image signal by performing predetermined signal processing on an imaging signal output from the sensor unit 244*a*. For example, the image processing unit 402 performs at least one of optical black reduction processing, white balance adjustment processing, color matrix calculation processing, gamma correction processing, color reproduction processing, and enhancement processing.

The input unit 403 receives input of various instructions including an operation instruction instructing that an operation of the endoscope system 1 be performed. The input unit 403 outputs a signal corresponding to the received instruction to the control unit 405. The recording unit 404 is a medium on which data including various programs for operating the endoscope system 1 and various parameters necessary for the operation of the endoscope system 1 is recorded. For example, the recording unit 404 is a flash memory or a dynamic random access memory (DRAM).

The control unit 405 controls configurations including the endoscope 2 and the light source device 3. For example, the control unit 405 controls the illumination unit 31 by outputting a control signal to the illumination control unit 32. The control unit 405 controls switching of light generated by the illumination unit 31. The control unit 405 controls the solid-state imaging device 244 by outputting a control signal to the imaging control unit 244*d*. The control unit 405 controls the voltage output from the power supply 401. The control unit 405 controls the voltage applied to the transparent electrode 130 according to light generated by the illumination unit 31. For example, the control unit 405 is a central processing unit (CPU).

The display device 5 displays an image on the basis of an image signal generated by the processing device 4. For example, the display device 5 is a liquid crystal display or an organic electro luminescence (EL) display.

The solid-state imaging device 245 of the second embodiment or the solid-state imaging device 246 of the third embodiment may be used instead of the solid-state imaging device 244.

The solid-state imaging device 244 used in the endoscope system 1 of the fourth embodiment need not have the input terminal 244*h* and the voltage generation circuit 244*c*. That is, the first voltage and the second voltage may be directly input to the solid-state imaging device 244.

The control unit 405 causes the illumination unit 31 to generate white light and causes the power supply 401 to generate the first voltage. Alternatively, the control unit 405 causes the illumination unit 31 to generate white light and causes the voltage generation circuit 244*c* to generate the first voltage. The control unit 405 causes the illumination unit 31 to generate narrowband light and causes the power supply 401 to generate the second voltage. Alternatively, the control unit 405 causes the illumination unit 31 to generate narrowband light and causes the voltage generation circuit 244*c* to generate the second voltage.

As described above, the endoscope system 1 includes the solid-state imaging device 244, the illumination unit 31 (illumination device), and the control unit 405 (control device). The illumination unit 31 generates white light and narrowband light having a wavelength shorter than 450 nm. The control unit 405 controls the voltage applied to the transparent electrode 130 according to the light generated by the illumination unit 31. When the illumination unit 31 generates white light, the first voltage is applied to the transparent electrode 130. When the illumination unit 31 generates narrowband light, the second voltage is applied to the transparent electrode 130.

The endoscope system of each aspect of the present invention need not have a configuration corresponding to at least one of the display device 5, the operation unit 22, and the universal cord 23. The endoscope system of each aspect of the present invention need not have a configuration corresponding to at least one of the light guide 241, the illumination lens 242, the imaging optical system 243, and the imaging control unit 244*d*. The endoscope system of each aspect of the present invention need not have a configuration corresponding to at least one of the illumination control unit 32, the power supply 401, the image processing unit 402, the input unit 403, and the recording unit 404.

In the fourth embodiment, the solid-state imaging device 244 can selectively detect narrowband light and light having a wavelength longer than the narrowband light, similar to the first embodiment. Accordingly, the endoscope system 1 can selectively detect the narrowband light and light having a wavelength longer than the narrowband light.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A backside illumination type solid-state imaging device, comprising:
   a semiconductor layer having a first surface, a second surface, and a plurality of photoelectric conversion elements;
   an electrode disposed on the first surface;
   a wiring layer laminated on the second surface of the semiconductor layer;
   a plurality of filters arranged on the first surface side at positions corresponding to the plurality of photoelectric conversion elements;
   an input terminal to which a reference voltage is input from outside; and
   a voltage generation circuit configured to generate a first voltage and a second voltage on the basis of the reference voltage input to the input terminal,
   wherein the plurality of filters include a first filter and a second filter,
   a light transmittance of the first filter has a peak in a wavelength range corresponding to blue,
   a light transmittance of the second filter has a peak at a wavelength of 450 nm or more, and in the second filter, a transmittance of light having a wavelength of 450 nm or less is greater than a minimum value of a transmittance of light having a wavelength longer than 450 nm,
   the first voltage and the second voltage are selectively applied to the electrode,
   the second voltage differs from the first voltage,
   the voltage generation circuit is configured to generate the second voltage to cause the photoelectric conversion elements to have a higher sensitivity to light having a wavelength of 450 nm or less, compared to when the first voltage is applied to the electrode,
   a potential in a cross section of the semiconductor layer has a first distribution when the first voltage is applied to the electrode,
   the potential in the cross section of the semiconductor layer has a second distribution when the second voltage is applied to the electrode,
   in a first region of the cross section of the semiconductor layer, the potential at a peak of the first distribution is greater than the potential at a peak of the second distribution, the first region is a region in which a distance from the first surface is less than 0.3 µm,
   a material constituting the semiconductor layer includes silicon,
   in the first distribution, a gradient of a variation of the potential in a second region of the cross section of the semiconductor layer is greater than a gradient of a variation of the potential in a third region,
   the second region is a region in which the distance is greater than a first distance at the peak of the first distribution and is less than 0.3 µm, and
   the third region is a region between the first surface and the photoelectric conversion elements in which the distance is 0.3 µm or more.

2. The backside illumination type solid-state imaging device according to claim 1, wherein a trench is arranged on the first surface side of the semiconductor layer in a region corresponding to a boundary between the first filter and the second filter.

3. An endoscope system, comprising:
   a backside illumination type solid-state imaging device including:
      a semiconductor layer having a first surface, a second surface, and a plurality of photoelectric conversion elements;
      an electrode disposed on the first surface;
      a wiring layer laminated on the second surface of the semiconductor layer; and
      a plurality of filters arranged on the first surface side at positions corresponding to the plurality of photoelectric conversion elements,
      wherein the plurality of filters include a first filter and a second filter, a light transmittance of the first filter has a peak in a wavelength range corresponding to blue, a light transmittance of the second filter has a peak at a wavelength of 450 nm or more, in the second filter, a transmittance of light having a wavelength of 450 nm or less is greater than a minimum value of a transmittance of light having a wavelength longer than 450 nm, a first voltage and a second voltage are selectively applied to the electrode, and the second voltage differs from the first voltage;
   an illumination device configured to generate white light and narrowband light having a wavelength shorter than 450 nm; and
   a control device configured to control a voltage that is applied to the electrode according to light generated by the illumination device,
   wherein the first voltage is applied to the electrode when the illumination device generates the white light,
   the second voltage is applied to the electrode when the illumination device generates the narrowband light, and
   the second voltage is applied to the electrode to cause the photoelectric conversion elements to have a higher sensitivity to light having a wavelength of 450 nm or less, compared to when the first voltage is applied to the electrode.

4. The endoscope system according to claim 3, wherein a potential in a cross section of the semiconductor layer has a first distribution when the first voltage is applied to the electrode,
   the potential in the cross section of the semiconductor layer has a second distribution when the second voltage is applied to the electrode,
   in a first region of the cross section of the semiconductor layer, the potential at a peak of the first distribution is greater than the potential at a peak of the second distribution, and
   the first region is a region in which a distance from the first surface is less than 0.3 µm.

5. The endoscope system according to claim 4, wherein a material constituting the semiconductor layer includes silicon, in the first distribution, a gradient of a variation of the potential in a second region of the cross section of the semiconductor layer is greater than a gradient of a variation of the potential in a third region of the cross section of the semiconductor layer, the second region is a region in which the distance is greater than a first distance at the peak of the first distribution and is less than 0.3 μm, and the third region is a region between the first surface and the photoelectric conversion elements in which the distance is 0.3 μm or more.

\* \* \* \* \*